United States Patent [19]

Adams et al.

[11] Patent Number: 5,304,139
[45] Date of Patent: Apr. 19, 1994

[54] IMPROVED LEAD CONFIGURATION FOR AN ATRIAL DEFIBRILLATOR

[75] Inventors: John M. Adams, Issaquah; Clifton A. Alferness, Redmond, both of Wash.

[73] Assignee: InControl, Inc., Redmond, Wash.

[21] Appl. No.: 924,109

[22] Filed: Aug. 3, 1992

Related U.S. Application Data

[62] Division of Ser. No. 685,130, Apr. 12, 1991, Pat. No. 5,282,837.

[51] Int. Cl.⁵ .............................................. A61N 1/05
[52] U.S. Cl. ........................................ 607/122; 607/5
[58] Field of Search ................. 128/419 D, 642, 783, 128/784, 786

[56] References Cited

U.S. PATENT DOCUMENTS

| | | | |
|---|---|---|---|
| 4,355,646 | 10/1982 | Kallok et al. | 128/786 |
| 5,165,403 | 11/1992 | Mehra | 128/419 D |
| 5,174,288 | 12/1992 | Bardy et al. | 128/786 |

Primary Examiner—William E. Kamm
Assistant Examiner—Kennedy J. Schaetzle
Attorney, Agent, or Firm—Foley & Lardner

[57] ABSTRACT

An implantable atrial defibrillator provides a pulse of defibrillating electrical energy to the atria of the heart in synchronism with sensed R waves in response to non-coincident sensing of an R wave at first and second areas of the heart. The defibrillating pulse is provided after a predetermined number of consecutive R waves are non-coincidently sensed to assure reliable synchronization. The atrial defibrillator is also operational in a marker mode wherein a number of synchronization marker pulses are delivered to the heart for detection on an externally generated electrocardiogram. The atrial fibrillation detector of the defibrillator is normally disabled and is activated when the sensed ventricular activity indicates a probability of atrial fibrillation to conserve a depletable power source. An endocardial lead is also described which ensures that the delivered atrial defibrillating electrical energy is substantially confined to the atria of the heart.

5 Claims, 7 Drawing Sheets

IMPROVED LEAD CONFIGURATION FOR AN ATRIAL DEFIBRILLATOR

This is a divisional of copending application Ser. No. 07/685,130 filed Apr. 12, 1991, now U.S. Pat. No. 5,282,837.

BACKGROUND OF THE INVENTION

The present invention generally relates to an atrial defibrillator for delivering a pulse of defibrillating electrical energy to the atria of a human heart. The present invention is more particularly directed to a fully automatic implantable atrial defibrillator which exhibits reduced power consumption, reliable synchronized delivery of defibrillating electrical energy to the atria, and multiple modes of operation including bradycardia pacing. The present invention is further directed to an improved endocardial lead for delivering the defibrillating electrical energy to the atria while minimizing the electrical energy applied to the ventricles.

Atrial fibrillation is probably the most common cardiac arrythmia. Although it is not usually a life threatening arrhythmia, it is associated with strokes thought to be caused by blood clots forming in areas of stagnant blood flow as a result of prolonged atrial fibrillation. In addition, patients afflicted with atrial fibrillation generally experience palpitations of the heart and may even experience dizziness or even loss of consciousness.

Atrial fibrillation occurs suddenly and many times can only be corrected by a discharge of electrical energy to the heart through the skin of the patient by way of an external defibrillator of the type well known in the art. This treatment is commonly referred to as synchronized cardioversion and, as its name implies, involves applying electrical defibrillating energy to the heart in synchronism with a detected electrical activation (R wave) of the heart. The treatment is very painful and, unfortunately, most often only results in temporary relief for patients, lasting but a few weeks.

Drugs are available for reducing the incidence of atrial fibrillation. However, these drugs have many side effects and many patients are resistent to them which greatly reduces their therapeutic effect.

Implantable atrial defibrillators have been proposed to provide patients suffering from occurrences of atrial fibrillation with relief. Unfortunately, to date, none of these atrial defibrillators have become a commercial reality to the detriment of such patients.

Implantable atrial defibrillators proposed in the past have exhibited a number of disadvantages which probably has been the cause of these defibrillators from becoming a commercial reality. Two such defibrillators, although represented as being implantable, were not fully automatic, requiring human interaction for cardioverting or defibrillating the heart. Both of these defibrillators require the patient to recognize the symptoms of atrial fibrillation with one defibrillator requiring a visit to a physician to activate the defibrillator and the other defibrillator requiring the patient to activate the defibrillator from external to the patient's skin with a magnet.

Synchronizing the delivery of the defibrillating or cardioverting energy with an electrical activation (R wave) of the heart is important to prevent ventricular fibrillation. Ventricular fibrillation is a fatal arrythmia which can be caused by electrical energy being delivered to the heart at the wrong time in the cardiac cycle, such as during the T wave of the cycle. As a result, it is most desirable to sense electrical activations of the heart to generate synchronization pulses (or signals) in a manner which avoids detecting noise as an electrical activation. Unfortunately, implantable atrial defibrillators proposed to date have not provided either such noise immunity or any other means for assuring reliable synchronization.

Another measure for reducing the risk of inducing ventricular fibrillation during the delivery of defibrillating electrical energy to the atria of the heart is to reduce the amount of the electrical energy which is passed through the ventricles. In other words, it is advantageous to confine the electrical energy to the atria as much as possible.

Implantable defibrillators, in general, must be powered by a portable, depletable power sources, such as a battery. However, an automatic implantable atrial defibrillator which continuously monitors atrial activity of the heart and which continuously monitors for atrial fibrillation will consume so much power that frequent battery replacement, requiring explanting the defibrillator, would be necessary.

The atrial defibrillator of the present invention provides solutions to all of the above noted deficiencies in atrial defibrillators proposed to date and other features which obviate potential problems in implantable atrial defibrillators. In general, the atrial defibrillator of the present invention is fully automatic and provides reliable synchronization to electrical activations, both through noise immune electrical activation sensing and through a test mode which permits a physician to confirm reliable electrical activation sensing. The atrial defibrillator of the present invention also provides for conserving battery power by activating the atrial fibrillation detector only when the ventricular rate indicates a probability of atrial fibrillation. In addition, the atrial defibrillator of the present invention provides a new and improved endocardial lead and a method for using the same which assures that the delivered electrical energy is confined to the atria and little of the electrical energy is passed through the ventricles.

SUMMARY OF THE INVENTION

The present invention provides an atrial defibrillator for applying an electrical defibrillating pulse to the atria of a human heart, wherein the atrial defibrillator is arranged to apply the electrical defibrillating pulse to the atria in synchronism with depolarization activation waves, and includes first means for sensing depolarization activation waves at a first area of the heart and second means for sensing the depolarization activation waves at a second area of the heart. The atrial defibrillator further includes means for detecting non-coincident sensing of a depolarization activation wave at the first area of the heart by the first means and at the second area of the heart by the second means, storage means for storing electrical energy, and delivery means coupled to the storage means and being responsive to the non-coincident sensing of a depolarization activation wave at the first and second areas of the heart for applying a predetermined amount of the stored electrical energy to the atria.

The present invention further provides an implantable atrial cardioverter arranged to be powered by a depletable power source for delivering electrical energy to the atria of a human heart in need of cardioversion. The atrial cardioverter includes sensing means for sensing electrical activations of the heart, wherein the sensing means is continuously operable, means responsive to the sensing means for determining the time intervals between the sensed electrical activations, and atrial arrythmia detector means for detecting the presence of an atrial arrythmia of the heart. The atrial arrythmia detecting means is normally disabled to avoid excessive consumption of the depletable power source. The atrial cardioverter further includes enable means for enabling the atrial arrythmia detector means responsive to the determined time intervals and delivery means responsive to the atrial arrythmia detector means for delivering the electrical energy to the atria of the heart in response to the atrial arrythmia detector means detecting an atrial arrythmia of the heart.

The present invention further provides an atrial defibrillator arranged to be implanted beneath the skin of a patient for applying electrical energy to the atria of a human heart. The atrial defibrillator includes sensing means for sensing electrical activations of the heart, first delivery means for delivering a first quantity of electrical energy to the atria of the heart in synchronism with one of the sensed electrical activations for cardioverting the heart, second delivery means for delivering at least one pulse of electrical energy to the heart in synchronism with one of the sensed electrical activations, wherein the pulse of electrical energy is of insufficient quantity to cardiovert the heart so as to be detected on an electrocardiogram generated externally to the skin of the patient, and select means for selecting either the first delivery means or the second delivery means.

The present invention further provides an atrial defibrillator for applying an electrical defibrillating pulse to the atria of a human heart in synchronism with an electrical activation of the heart. The atrial defibrillator includes sensing means for sensing electrical activations of the heart, synchronizing pulse generating means responsive to the sensing means for generating a synchronizing pulse for each sensed electrical activation, and counting means for counting the synchronizing pulses provided by the synchronizing pulse generating means. The atrial defibrillator also includes delivery means responsive to the counting means for applying the electrical defibrillating pulse to the atria after a predetermined number of the synchronizing pulses have been counted by the counter means and in response to the last one of the predetermined number of synchronizing pulses.

The present invention further provides an intravascular lead for use in association with an atrial defibrillator of the type arranged to cardiovert the atria of the human heart. The lead includes a distal end and a proximal end, the proximal end including connector means arranged to be received by the atrial defibrillator, and wherein the connector means includes first, second, and third contacts. The lead further includes a first electrode at the distal end, a second electrode proximal to the first electrode, and a third electrode proximal to the second electrode. The lead, further includes conductor means for electrically connecting the first contact to the first electrode, the second contact to the second electrode, and the third contact to the third electrode and the lead being flexible so as to be arranged to be passed down the superior vena cava of the heart, into the right atrium, into the coronary sinus ostium, and advanced into the coronary sinus of the heart near the left side thereof. The electrodes are spaced apart such that when the first electrode is within the coronary sinus adjacent the left ventricle, the second electrode is beneath the left atrium near the left ventricle and the third electrode is within the right atrium or the superior vena cava.

The present invention further provides an implantable atrial defibrillator for applying an electrical defibrillating pulse to the atria of a human heart. The atrial defibrillator includes first means for sensing electrical activations of the heart at the right ventricle, second means for sensing electrical activations of the heart at the left ventricle, and enable means responsive to the first means for detecting an abnormal rhythm of the right ventricle and providing an enable control signal. The atrial defibrillator further includes atrial fibrillation detector means including atrial sensing means for sensing atrial activity of at least one of the atria, the atrial fibrillation detector means being arranged to be activated by the enable control signal for detecting atrial fibrillation of the heart, and storage means for storing the electrical energy responsive to the atrial fibrillation detector means detecting atrial fibrillation. The atrial defibrillator further includes delivery means responsive to the atrial fibrillation detector means, coupled to the storage means, and being responsive to non-coincident sensing of an electrical activation by said first and second means for applying a predetermined amount of the stored electrical energy to the atria of the heart.

The present invention further provides a method of applying electrical defibrillating energy to the atria of a human heart while minimizing the electrical energy applied to the right and left ventricles. The method includes the steps of providing a first electrode, establishing electrical contact between the first electrode and point within the coronary sinus beneath the left atrium, providing a second electrode, establishing electrical contact between the second electrode and a region adjacent to the right atrium, and applying defibrillating electrical energy between the first and second electrodes.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawing, in the several figures of which like reference numerals identify identical elements, and wherein:

DETAILED DESCRIPTION OF THE PREFERRED EMBODIMENT

Figure 1:
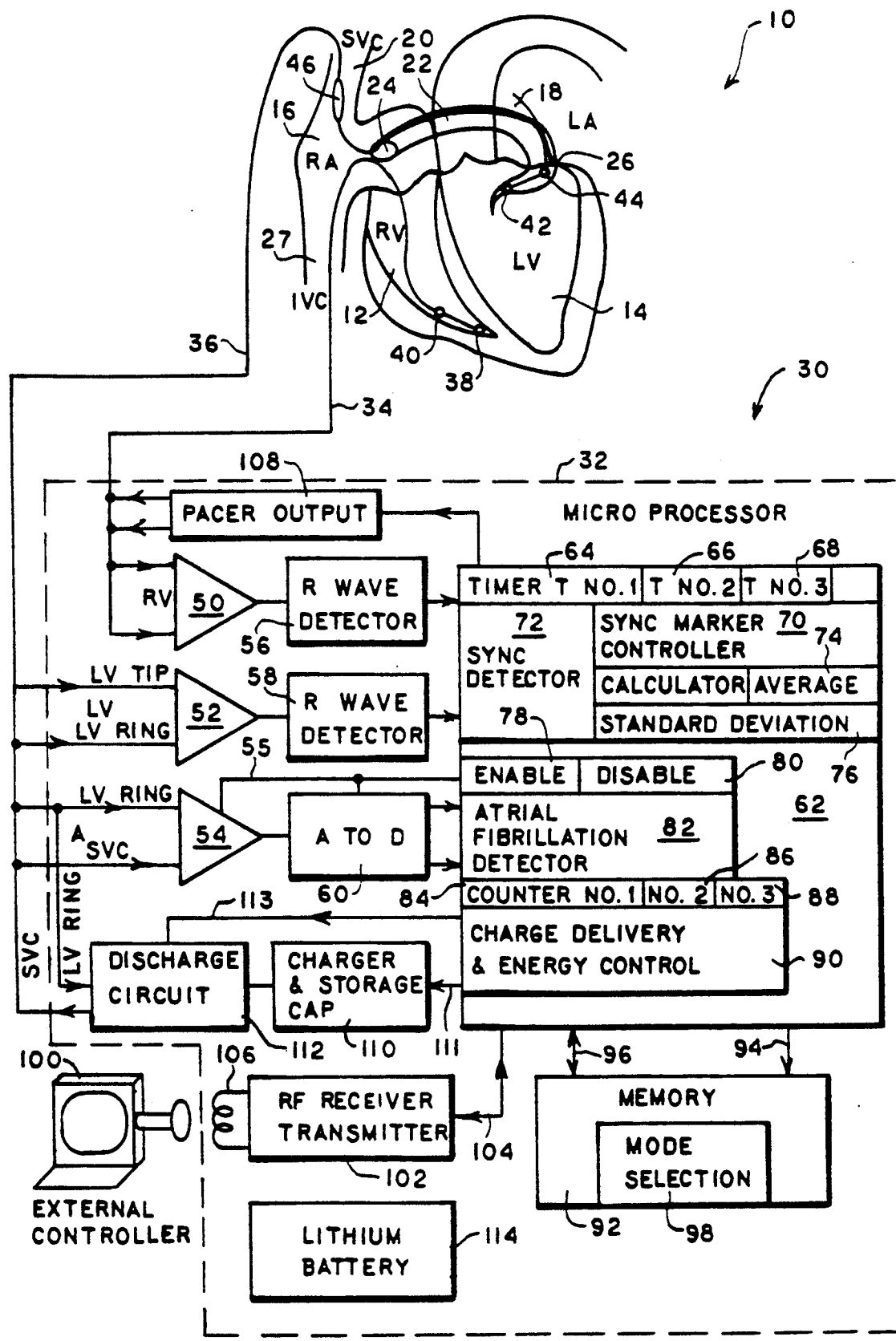
FIG. 1 is a schematic block diagram of a fully implantable atrial defibrillator embodying the present invention for applying defibrillating electrical energy to the atria of a human heart and which is shown in association with a human heart in need of atrial fibrillation monitoring and potential cardioversion of the atria.

Referring now to FIG. 1, it illustrates a fully implantable atrial defibrillator 30 embodying the present invention shown in association with a schematically illustrated human heart 10 in need of atrial fibrillation monitoring and potential cardioversion of the atria. The portions of the heart 10 illustrated in FIG. 1 are the right ventricle 12, the left ventricle 14, the right atrium 16, the left atrium 18, the superior vena cava 20, the coronary sinus 22, the coronary sinus ostium or opening 24, the left ventricular free wall 26 and the inferior vena cava 27. In addition, as used herein, the term "electrical activations" denotes R waves of the heart cardiac cycle which induce depolarizations of the ventricles 12 and 14.

The atrial defibrillator 30 generally includes an enclosure 32 for hermetically sealing the internal circuit elements of the atrial defibrillator to be described hereinafter, an endocardial first lead 34, and an intravascular second lead 36. The enclosure 32 and first and second leads 34 and 36 are arranged to be implanted beneath the skin of a patient so as to render the atrial defibrillator 30 fully implantable.

The endocardial first lead 34 preferably comprises a endocardial bi-polar lead having electrodes 38 and 40 arranged for establishing electrical contact with the right ventricle 12 of the heart 10. The electrodes 38 and 40 permit bi-polar sensing of electrical activations in the right ventricle. As illustrated, the lead 34 is fed through the inferior vena cava 27, into the right atrium 16, and then into the right ventricle 12 as illustrated. As will be appreciated by those skilled in the art, a second path for lead 34 could alternatively be through the superior vena cava 20, into the right atrium 16, and then into the right ventricle 12.

The second lead 36, which will be described in greater detail with respect to FIGS. 7 and 8, generally includes a first or tip electrode 42, a second or ring electrode 44, and a third electrode 46. As illustrated, the second lead 36 is flexible and arranged to be passed down the superior vena cava 20, into the right atrium 16, into the coronary sinus ostium 24, and advanced into the coronary sinus 22 of the heart near the left side thereof so that the first or tip electrode 42 is within the coronary sinus adjacent the left ventricle 14. The electrodes 42, 44, and 46 are spaced apart such that when the first electrode 42 is within the coronary sinus 22 adjacent the left ventricle 14, the second electrode 44 is beneath the left atrium 18 near the left ventricle 14 and the third electrode 46 is in a region adjacent to the right atrium coronary sinus ostium 24 within either the right atrium 16 or the superior vena cava 20. The first electrode 42 and the second electrode 44 enable bi-polar sensing of electrical activations of the left ventricle 14. The second electrode 44 together with the third electrode 46 provide bi-polar sensing of heart activity in the atria 16 and 18. The second electrode 44 and the third electrode 46 further provide for the delivery of defibrillating electrical energy of the atria. Because the second electrode 44 is located beneath the left atrium 18 near the left ventricle 14 and the third electrode 46 is within either the right atrium 16 or the superior vena cava 20 and above the coronary sinus ostium 24, the electrical energy applied between these electrodes will be substantially confined to the atria 16 and 18 of the heart 10. As a result, the electrical energy applied to the right ventricle 12 and left ventricle 14 when the atria are cardioverted or defibrillated will be minimized. This greatly reduces the potential for ventricular fibrillation of the heart to be induced as a result of the application of defibrillating electrical energy of the atria of the heart.

Within the enclosure 32, the atrial defibrillator 30 includes a first sense amplifier 50, a second sense amplifier 52, and a third sense amplifier 54. The first sense amplifier 50 forms a first sensing means which together with the first lead 34 to which it is coupled, senses electrical activations of the right ventricle 12. The second sense amplifier 52 forms a second sensing means which, together with the first electrode 42 and second electrode 44 of the second lead 36 to which it is coupled senses electrical activations of the left ventricle 14. The third sense amplifier 54 forms atrial sense means which, together with the second electrode 44 and third electrode 46 of the second lead 36 to which it is coupled senses atrial activity of the heart when enabled as will be described hereinafter.

The outputs of the first and second sense amplifiers 50 and 52 are coupled to first and second R wave detectors 56 and 58 respectively. Each of the R wave detectors 56 and 58 is of the type well known in the art which provides an output pulse upon the occurrence of an R wave being sensed during a cardiac cycle of the heart. The output of the third sense amplifier 54 is coupled to an analog to digital converter 60 which converts the analog signal representative of the atrial activity of the heart being sensed to digital samples for processing when the analog to digital converter 60 is enabled also in a manner to be described hereinafter.

The enclosure 32 of the atrial defibrillator 30 further includes a microprocessor 62. The microprocessor 62 is preferably implemented in a manner to be described hereinafter with respect to the flow diagrams of FIGS. 2 through 6. The implementation of the microprocessor 62 results in a plurality of functional stages. The stages include a first timer 64, a second timer 66, a third timer 68, a synchronization marker controller 70, and a synchronization detector 72. The functional stages of the microprocessor 62 further include a calculator stage including an average calculation stage 74, a standard deviation calculation stage 76, an enable stage 78, a disable stage 80, an atrial arrythmia detector in the form of an atrial fibrillation detector 82, a first counter 84, a second counter 86, a third counter 88, and a charge delivery and energy control stage 90.

The microprocessor 62 is arranged to operate in conjunction with a memory 92. The memory 92 is coupled to the microprocessor 62 by a multiple-bit address bus 94 and a bi-directional multiple-bit databus 96. The address bus 94 permits the microprocessor 62 to address desired memory locations within the memory 92 for executing write or read operations. During a write operation, the microprocessor stores data, such as time intervals or operating parameters in the memory 92 at the addresses defined by the multiple-bit addresses conveyed over bus 94 and coveys the data to the memory 92 over the multiple-bit bus 96. During a read operation, the microprocessor 62 obtains data from the memory 92 from the storage locations identified by the multiple-bit addresses provided over bus 94 and receives the data from the memory 92 over the bi-directional bus 96.

For entering operating parameters into the memory 92, the microprocessor 62 receives programmable operating parameters from an external controller 100 which is external to the skin of the patient. The external controller 100 is arranged to communicate with a receiver/transmitter 102 which is coupled to the microprocessor 62 over a bi-directional bus 104. The receiver/transmitter 102 may be of the type well known in the art for conveying various information which it obtains from the microprocessor 62 to the external controller 100 or for receiving programming parameters from the external controller 100 which the receiver/transmitter 102 then conveys to the microprocessor 62 for storage in the memory 92. To that end, the memory 92 includes a mode selection portion 98 for storing mode selection information to be described hereinafter.

The receiver/transmitter 102 includes a transmitting coil 106 so that the receiver/transmitter 102 and coil 106 form a communication means. Such communication means are well known in the art and may be utilized as noted above for receiving commands from external to the implantable enclosures 32 and for transmitting data to the external controller 100 from the implanted enclosure 32. One such communication system is disclosed, for example, in U.S. Pat. No. 4,586,508.

To complete the identification of the various structural elements within the enclosure 32, the atrial defibrillator 30 further includes a pacer output stage 108. As will be seen hereinafter, the pacer output stage 108 applies stimulating pulses to the right ventricle 12 of the heart 10 when bradycardia pacing is required or synchronization marker pulses to the right ventricle when the atrial defibrillator is in the marker pulse mode. The atrial defibrillator 30 further includes a charger and storage capacitor circuit 110 of the type well known in the art which charges a storage capacitor to a predetermined voltage level and a discharge circuit 112 for discharging the storage capacitor within circuit 110 by a predetermined amount to provide a controlled discharge output of electrical energy when required to the atria of the heart. To that end, the discharge circuit 112 is coupled to the second electrode 44 and the third electrode 46 of the second lead 36 for applying the cardioverting or defibrillating electrical energy to the atria. Lastly, the defibrillator 30 includes a depletable power source 114, such a lithium battery, for providing power to the electrical components of the atrial defibrillator 30. As will be seen hereinafter, the atrial defibrillator 30 is arranged to minimize the power consumption of the battery 114 so as to extend the useful life of the atrial defibrillator 30.

Figure 2:
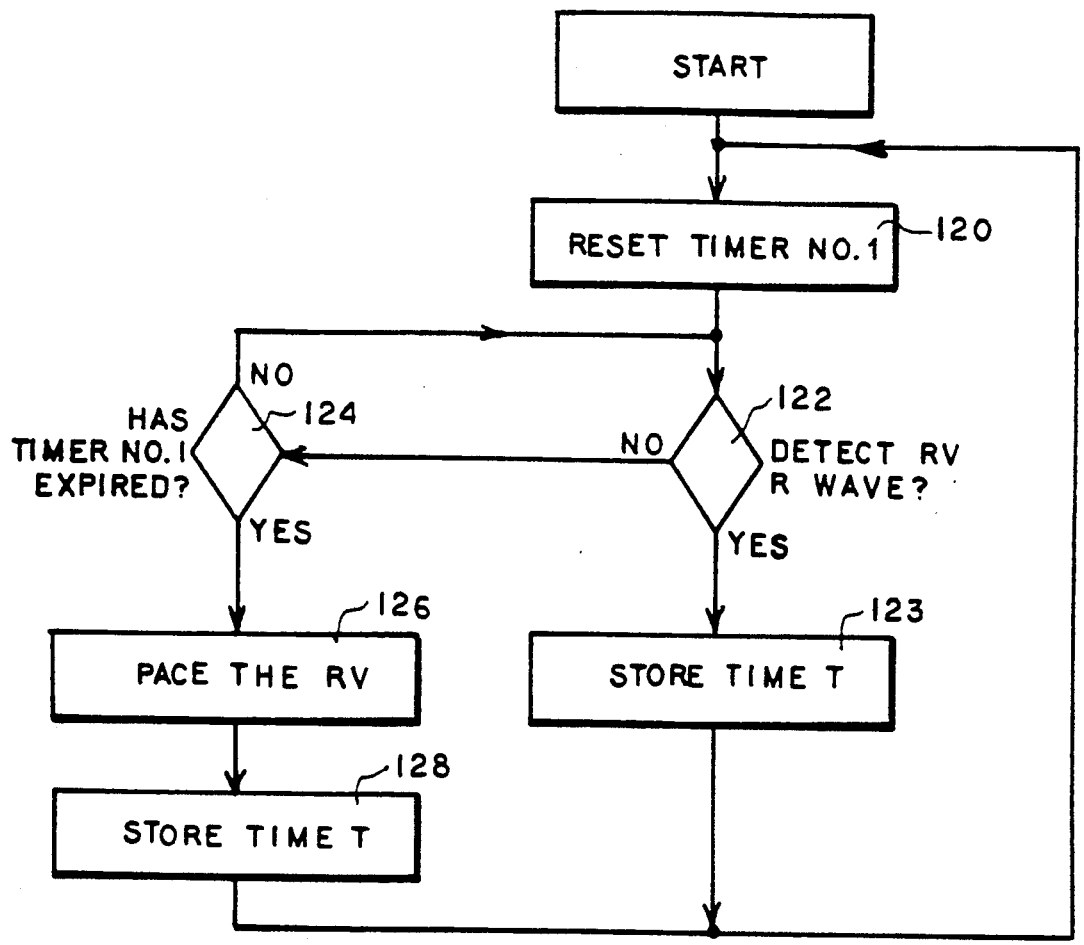
FIG. 2 is a flow diagram illustrating the manner in which the atrial defibrillator of FIG. 1 may be implemented in accordance with the present invention for providing bradycardia pacing of the right ventricle of the heart and for determining and storing the time intervals between depolarizations of the right ventricle.

The operation of the atrial defibrillator 30 and more particularly the operation of the functional stages residing within the enclosure 32 will now be described with reference to the flow diagrams of FIGS. 2–6. Referring now to FIG. 2, it illustrates the manner in which the atrial defibrillator 30 may be implemented in accordance with the present invention for providing bradycardia pacing of the right ventricle 12 of the heart 10 and the determining of the time intervals between electrical activations of the right ventricle or bradycardia pacing pulses of the right ventricle. This process begins with the resetting of the first timer 64 in step 120. The microprocessor then, in step 122, determines whether an R wave has been detected at the right ventricle. If an R wave has not been detected at the right ventricle, the processor then determines in step 124 if the first timer 64 has expired. If the first timer 64 has not expired, the processor returns to step 122 to determine whether an R wave has been detected at the right ventricle. If an R wave or electrical activation has been detected at the right ventricle, the processor then in step 123 determines the time (T) since the first timer 64 was last reset and stores that time interval in the memory 92. The processor then returns to step 120 to reset the first timer 64.

If in step 124 the processor had determined that the first timer 64 had expired, it would proceed to step 126 to pace the right ventricle. In so doing, the microprocessor activates the pacer output 108 and causes the pacer output 108 to provide an electrical stimulating pulse to the electrodes 38 and 40 of the first lead 34. The timeout time of the first timer 64 may be, for example, one second and may be programmed into the memory 92 through the external controller 100 and the receiver/transmitter 102.

Upon the pacing of the right ventricle in step 126, the processor then in step 128 determines the time on the first timer 64 and stores that time as a determined time interval. The processor then returns to step 120 to once again reset the first timer.

As can thus be seen, the atrial defibrillator 30 provides bradycardia pacing of the right ventricle 12 and, upon each electrical activation being sensed at the right ventricle, determines the time interval since the first timer 64 was reset by either a sensed electrical activation of the right ventricle or a stimulating pulse being delivered to the right ventricle during bradycardia pacing. Hence, in determining the time intervals, the sensed electrical activations of the right ventricle and the delivery of a stimulating pacing pulse to the right ventricle are considered to be equivalent events in that each results in a depolarization of the right ventricle.

Figure 3:
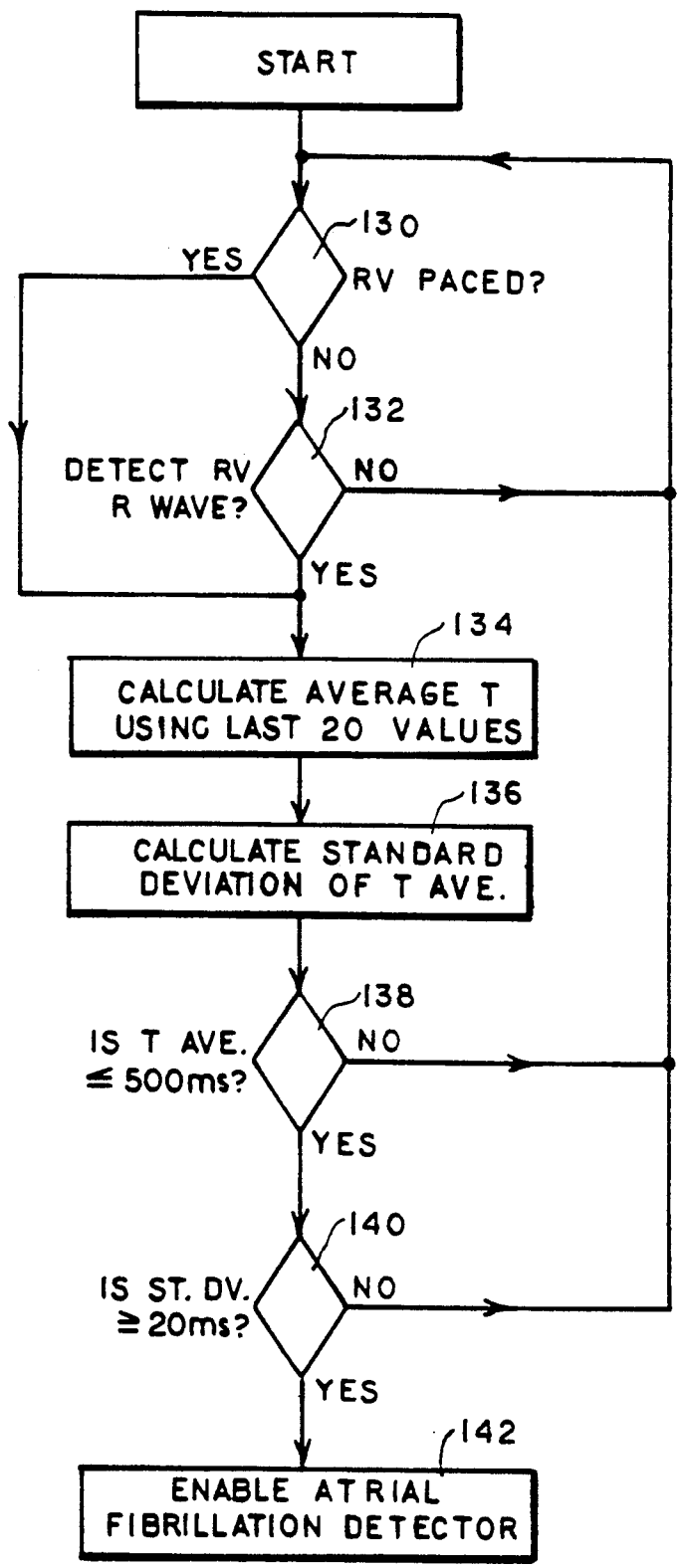
FIG. 3 is a flow diagram illustrating the manner in which the atrial defibrillator of FIG. 1 may be implemented in accordance with the present invention for enabling the atrial fibrillation detector of the atrial defibrillator.

Referring now to FIG. 3, it illustrates the manner in which the atrial defibrillator 30 may be implemented for enabling the atrial fibrillation detector 82. This process begins at step 130 wherein the microprocessor first determines whether the right ventricle has been paced by the pacer output 108. If the right ventricle has not been paced, the processor proceeds to step 132 to determine whether an R wave has been detected at the right ventricle. If an R wave has not been detected at the right ventricle, the processor returns to step 130 to once again determine whether the right ventricle has been paced. If the right ventricle has been paced as determined in step 130 or if an R wave has been detected at the right ventricle in step 132, the processor then proceeds to step 134 to calculate an average time interval using the last 20 stored time interval values. This is performed by the average calculation stage 74 of the microprocessor 62.

After calculating the average time interval over the last twenty stored values of the time interval, the processor then proceeds to step 136 to calculate the standard deviation of the average time interval calculated in step 134 for the last twenty stored values of the time interval. The standard deviation is calculated in the standard deviation calculation stage 76.

After calculating both the average time interval for the last twenty stored values of the time interval and the standard deviation for the average time interval for the last twenty stored values of the time interval, the processor then proceeds to step 138 to determine if the average time interval calculated in step 134 is less than or equal to a first predetermined time interval of, for example, 500 milliseconds. If the average time interval calculated in step 134 is not less than or equal to 500 milliseconds, the processor then returns to step 130 to once again determine whether the right ventricle has been paced.

If in step 138 the processor determines that the average time interval calculated in step 134 is less than or equal to 500 milliseconds, the processor then proceeds to step 140 to determine if the standard deviation calculated in step 136 is greater than or equal to a predetermined standard deviation of, for example, twenty milliseconds. If the standard deviation calculated in step 136 is not greater than or equal to twenty milliseconds, the processor returns to step 130 to once again determine whether the right ventricle has been paced. However, if the standard deviation calculated in step 136 is greater than or equal to the predetermined standard deviation of, for example, twenty milliseconds, the processor then proceeds to step 142 to enable the atrial fibrillation detector. This step is performed through the enable stage 78 which enables the atrial fibrillation detector 82, the analog-to-digital converter 60, and the third sense amplifier 54 over a control line 55. This causes the atrial fibrillation detector 82, the analog-to-digital converter 60, and the third sense amplifier 54 to be activated.

As can thus be seen by the implementation illustrated in FIG. 3, the atrial defibrillator 30 activates the atrial fibrillation detector 82, the analog-to-digital converter 60, and the third sense amplifier 54 responsive to the determined time intervals, and preferably, the last twenty time intervals stored in the memory 92. This allows the atrial fibrillation detector 82, the analog-to-digital converter 60, and the third sense amplifier 54 to be normally disabled to avoid excessive consumption of the battery 114. This is particularly important because the algorithms utilized in arrythmia detectors, such as fibrillation detectors, consume considerable power and if left continuously energized, would require frequent replacement of the defibrillators in which they are employed for the purpose of replacing the depletable power sources, such as a battery.

The criteria utilized for activating the atrial fibrillation detector is both the average heart rate and the variability of the heart rate. By utilizing this criteria, the atrial fibrillation detector need only be activated when there is a probability that atrial fibrillation is present to thus permit the atrial fibrillation detector, the analog-to-digital converter 60, and the third sense amplifier 54 to be normally disabled for conserving the power of the depletable power source.

Thus far, it will also be noted that only the right ventricle is being sensed. Only electrical activations of the right ventricle are sensed for either providing bradycardia pacing of the right ventricle or for enabling the atrial fibrillation detector. This assures that little power is consumed during the times in which neither bradycardia pacing is required or in which there is a low probability that atrial fibrillation is present in the heart.

In accordance with this preferred embodiment, the atrial fibrillation detector 82, the analog-to-digital converter 60, and the third sense amplifier 54 may also be activated manually from external to the patient's skin. This external activation may be accomplished by, for example, the patient's physician sending suitable commands from the external controller 100. The commands would then be received by the receiver/transmitter 102 and conveyed to the microprocessor 62 which would then, in response to the received command, activate the atrial fibrillation detector 82, the analog-to-digital converter 60, and the third sense amplifier 54.

Figure 4:
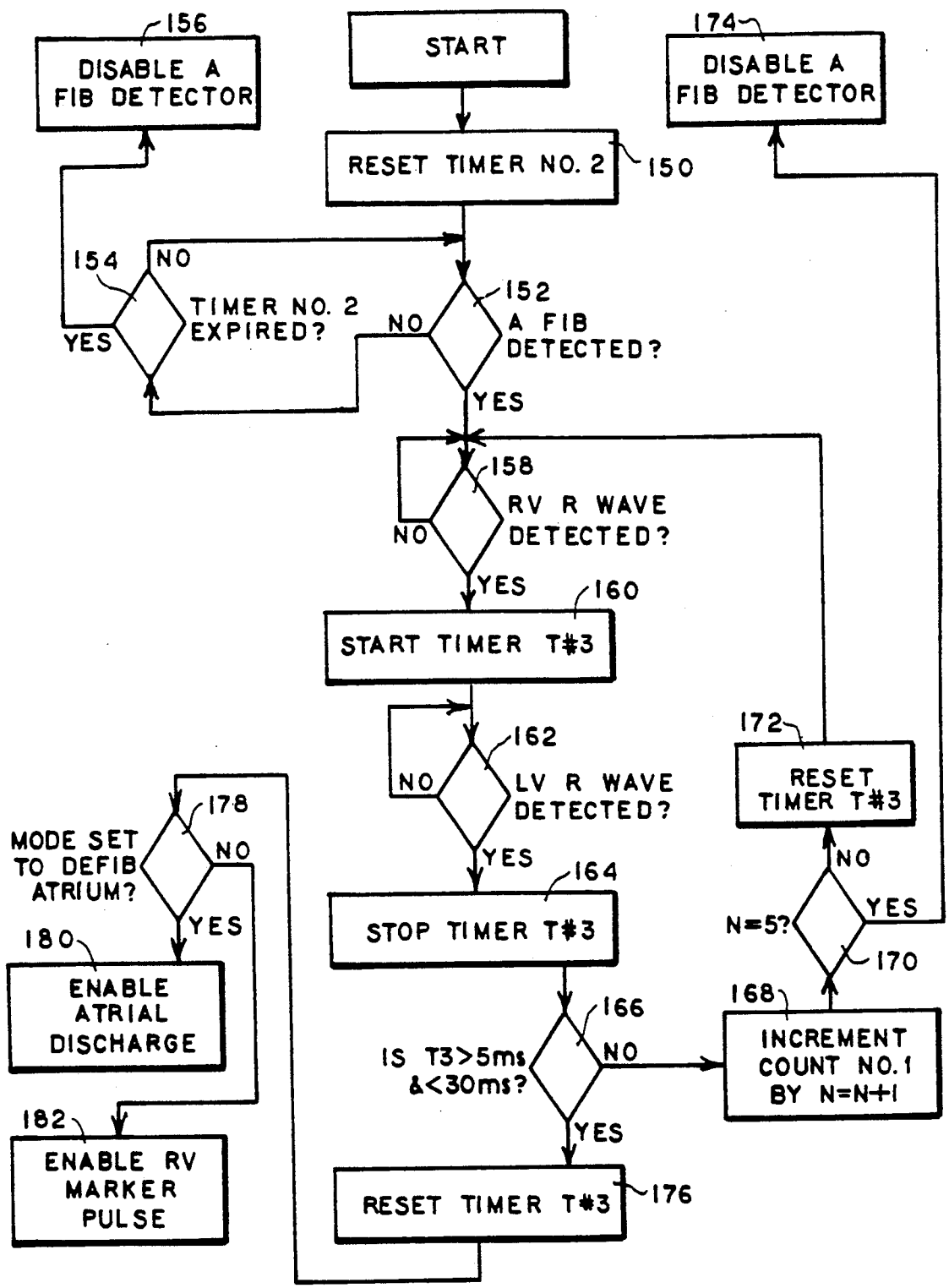
FIG. 4 is a flow diagram illustrating the manner in which the atrial defibrillator of FIG. 1 may be implemented in accordance with the present invention for detecting atrial fibrillation and enabling either the atrial defibrillating output or the right ventricle marker pulse output.

Referring now to FIG. 4, it illustrates the manner in which the atrial defibrillator 30 may be implemented for detecting the occurrence of atrial fibrillation in the heart and for enabling either the atrial defibrillation output or the right ventricle marker output of the atrial defibrillator.

This process begins at step 150 wherein the microprocessor resets the second timer 66. The processor then proceeds to step 152 to determine whether atrial fibrillation is detected. Here it is assumed that the average time interval calculated in step 134 for the last twenty values of the stored time intervals was less than or equal to 500 milliseconds and that the standard deviation of the average time interval for the last twenty stored values of the time intervals was greater than 20 milliseconds as calculated in step 136 and determined in step 140 to cause the atrial fibrillation detector 82, the analog to digital converter 60, and the third sense amplifier 54 to be activated by the control line 55. Atrial fibrillation may be detected by the microprocessor through processing the digitized values of the atrial activity provided by the analog to digital converter 60. As previously mentioned, the atrial activity is sensed by the second electrode 44 and third electrode 46 of the second lead 36 and the third sense amplifier 54.

There are many algorithms known in the art for processing such data to determine if fibrillation is present. One such algorithm is disclosed in a paper: Nitish V. Thakor, Yi-Sheng Zhu and Kong-Yan Pan, "Ventricular Tachycardia and Fibrillation Detection by a Sequential Hypothesis Testing Algorithm," *IEEE Transactions On Biomedical Engineering,*" Vol. 37, No. 9, pp. 837–843, September 1990. Implementing such an algorithm by a microprocessor such as microprocessor 62 is well within the preview of one skilled in the art.

If in step 152 it is determined that atrial fibrillation is not currently taking place in the heart, the microprocessor then proceeds to step 154 to determine whether the second timer 66 has expired. If the second timer has not expired, the processor returns to step 152 to again determine whether atrial fibrillation is currently taking place in the heart. If in step 154 it is determined that the second timer 66 has expired, the processor then proceeds to step 156 to disable the atrial fibrillation detector. This step is performed after a predetermined expiration time of the timer 66, which may be, for example, six seconds.

If the atrial defibrillator in step 152 determines that atrial fibrillation is currently present in the heart, the microprocessor then proceeds to determine whether it is able to obtain a reliable synchronizing pulse for synchronizing the delivery of the defibrillating or cardioverting electrical energy to the atria. This begins in step 158 where the atrial defibrillator microprocessor determines whether an electrical activation has been detected in the right ventricle. If an R wave has not been detected in the right ventricle, the microprocessor performs a loop to once again determine at step 158 if an R wave has been detected in the right ventricle. When an R wave is detected in the right ventricle, the microprocessor proceeds to step 160 to start the third timer 68. After starting timer 68, the processor then proceeds to step 162 to determine whether an R wave has been detected in the left ventricle. If an electrical activation has not been detected at the left ventricle, the microprocessor then returns to step 162 to once again determine whether an R wave has been detected at the left ventricle. When an R wave is detected at the left ventricle, the microprocessor then proceeds to step 164 to stop the third timer 68. In so doing, the third timer 68 will have the time from when the R wave was detected at the right ventricle in step 158 and when the same R wave was detected at the left ventricle in step 162.

The microprocessor then proceeds to step 166 to determine if the time between the detection of the electrical activation at the right ventricle and at the left ventricle is within a range of normal delay times between depolarization activation waves being sensed at the right ventricle and the left ventricle. The predetermined range may be established by programming the range into the memory 92 from the external controller, through the receiver/transmitter 102 and the microprocessor 62. The normal delay times may, for example, range from 5 milliseconds to 30 milliseconds. As a result, in step 166, the microprocessor determines whether the time between the sensing of the electrical activation and the right ventricle and in the left ventricle was greater than 5 milliseconds and less then 30 milliseconds. If it was not, this is considered to be a negative test resulting in an unreliable synchronizing detection. In this event, the microprocessor proceeds to step 168 to increment the first counter 84. The microprocessor then proceeds to step 170 to determine whether the count in the first counter 84 is equal to a predetermined count, of, for example, five. If it is not, the processor then resets the third timer 68 in step 172 and returns to step 158 to detect another R wave at the right ventricle for detecting whether a reliable synchronizing pulse may be detected. When the count within the first counter 84 reaches the predetermined count of five, the processor then proceeds to step 174 to disable the atrial fibrillation detector 82. Both this step and step 156 may be performed by the disable stage 80 providing a disable signal over the control line 55 for disabling the atrial fibrillation detector, the analog to digital converter 60, and the third sense amplifier 54.

As can be seen from the foregoing, the atrial defibrillator will go no further in its processing even though atrial fibrillation has been detected if it is not assured that a reliable synchronization pulse could be generated for synchronizing the delivery of the defibrillating or cardioverting electrical energy to the atria in synchronism with an electrical activation of the heart. This also, as will be seen hereinafter, negates the need for activating the charging circuit 110 for charging the storage capacitor if a defibrillating pulse could not be reliably applied in synchronism with an electrical activation of the heart to further conserve the depletable power source of the battery 114.

In determining whether a reliable synchronization pulse can be derived, and as will be seen hereinafter, in providing a synchronization pulse, the atrial defibrillator first senses a depolarization activation wave at a first area of the heart and senses the same depolarization activation wave at a second area of the heart. In accordance with this preferred embodiment, the first area of the heart is the right ventricle and the second area of the heart is the left ventricle. If the activation wave at the right and left ventricle is detected coincidently as will be determined in step 166, or detected at times too far apart to be considered a legitimate electrical activation wave, a synchronization pulse will not be derived nor will such detection be considered a positive test of the ability to derive such a synchronization pulse. The foregoing is based upon the fact electrical activation depolarization waves propagate across the heart so that the sensing of an electrical activation at two different areas of the heart should occur at different times while noise, which may be mistaken for an electrical activation, would be detected at both areas of the heart simultaneously. As a result, the non-coincident sensing of an electrical activation at two different areas of the heart such as at the right ventricle and the left ventricle provide a reliable indication that the sensed electrical activation is a real or legitimate electrical activation and can be relied upon for deriving a reliable synchronization pulse for synchronizing the delivery of a defibrillating or cardioverting electrical pulse to the atria in synchronism with an electrical activation of the heart.

Referring again to FIG. 4, if in step 166 it is determined that there has been non-coincident sensing of an electrical activation at the right ventricle and the left ventricle by determining that such sensing occurred within a time greater than 5 milliseconds and less than 30 milliseconds, the microprocessor proceeds to step 176 to reset the third timer 68. After resetting timer 68, the microprocessor then determines in step 178 if the atrial defibrillator is set in the defibrillating mode. In performing this step, the microprocessor accesses the contents of a known storage location in the mode selection portion 98 of memory 92 to determine, for example, if that bit is set or not set. For example, if the bit is set this may be considered by the microprocessor as indicating that the atrial defibrillator is set in the defibrillating mode. If the bit is not set, the microprocessor may consider this as indicating that the atrial defibrillator is in the right ventricle marker mode and not the atrial defibrillating mode. Hence, if it is determined in step 178 that the atrial defibrillator is in the atrial defibrillating mode, it will then in step 180 enable the charge delivery and energy control stage 90. If the atrial defibrillator is not in the atrial defibrillating mode, the microprocessor will then enable the sync marker controller 70 in step 182.

Figure 5:
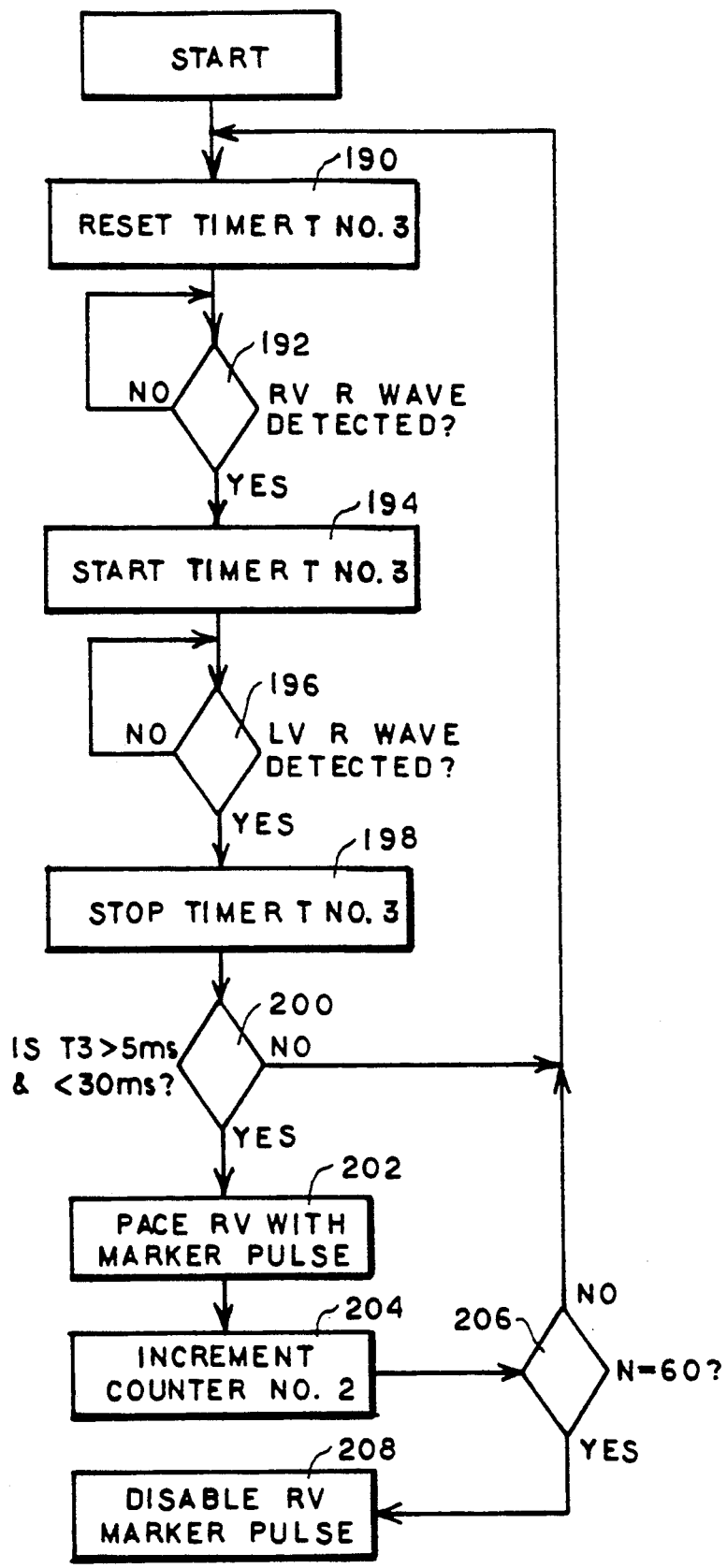
FIG. 5 is a flow diagram illustrating the manner in which the atrial defibrillator of FIG. 1 may be implemented in accordance with the present invention for providing right ventricle marker pulses in synchronism with detected electrical activations (R waves) of the heart.

Referring now to FIG. 5, it illustrates the manner in which the atrial defibrillator 30 may be implemented for providing marker sync pulses to the right ventricle 12 of the heart 10. The foregoing assumes that in step 178, the microprocessor determined that the atrial defibrillator was in the marker pulse mode and has enabled the sync marker controller 70.

This process begins at step 190 with the microprocessor resetting the third timer 68. The microprocessor then proceeds to step 192 to determine whether an R wave has been detected at the right ventricle. If an R wave has not been detected, the microprocessor continues to determine whether an R wave has been detected at the right ventricle until an R wave is detected. When an R wave is detected at the right ventricle, the microprocessor then proceeds to step 194 to start the third timer 68. It then advances to step 196 to determine whether the R wave has been detected at the left ventricle. If the R wave has not been detected at the left ventricle, the microprocessor continues to determine whether an R wave has been detected at the left ventricle and when the R wave has been detected at the left ventricle, the microprocessor then at step 198 stops the third timer 68. After stopping timer 68, the microprocessor then proceeds to step 200 to determine if the time between the sensing of the R wave at the right ventricle and at the left ventricle occurred within a time greater than 5 milliseconds and less than 30 milliseconds. If it has not, the detected R wave is considered to be either noise or an unreliable detection and the microprocessor returns to step 190 to reset the third timer 68. If, however, the microprocessor determines in step 200 that the R wave was detected at the right ventricle and the left ventricle within the normal delay time range of 5 milliseconds and 30 milliseconds, the microprocessor then proceeds to step 202 to pace the right ventricle with a marker pulse. This step is performed by the sync detector 72 providing a sync pulse to the sync marker controller 70 and the sync marker controller 70 causing the pacer output 108 to pace the right ventricle.

After the right ventricle is paced with the marker pulse, the microprocessor proceeds to step 204 to increment the second counter 86. The microprocessor then proceeds to step 206 to determine whether the second counter 86 has reached a predetermined count of, for example, 60 marker pulses. If it has not, the microprocessor returns to step 190 to reset the third timer 68 and to detect another electrical activation of the heart for providing a synchronizing pulse. If the count in the second counter 86 has reached the predetermined number of marker pulses counted, such as 60 pulses, the microprocessor then proceeds to step 208 to disable the sync marker controller 70 and to terminate the provision of the marker pulses to the right ventricle.

As can be seen by the foregoing, the atrial defibrillator 30 is arranged to provide marker pulses to enable a physician to determine whether proper operating parameters have been established within the atrial defibrillator for reliably detecting electrical activations to provide reliable synchronizing pulses. The marker pulses provided to the right ventricle are preferably of a relatively low energy, and of an energy which is insufficient to cardiovert or defibrillate the heart but which may be sufficient for pacing the right ventricle of the heart. For example, the quantity of electrical energy utilized in each marker pulse may have an energy in the range of 5 to 50 microjoules and preferably 25 microjoules. Marker pulse energies of, for example, 25 microjoules, although being sufficient to pace the right ventricle of the heart, would not adversely affect normal heart rhythm in as much as the marker pulses are being provided in synchronism with detected electrical activations of the heart and more particularly, reliably detected activations of the heart in accordance with the present invention. The marker pulses, if applied in the range of energies noted above, will have energies sufficient so as to be detected on an electrocardiogram generated externally to the skin of the patient by a physician in a known manner.

Figure 6:
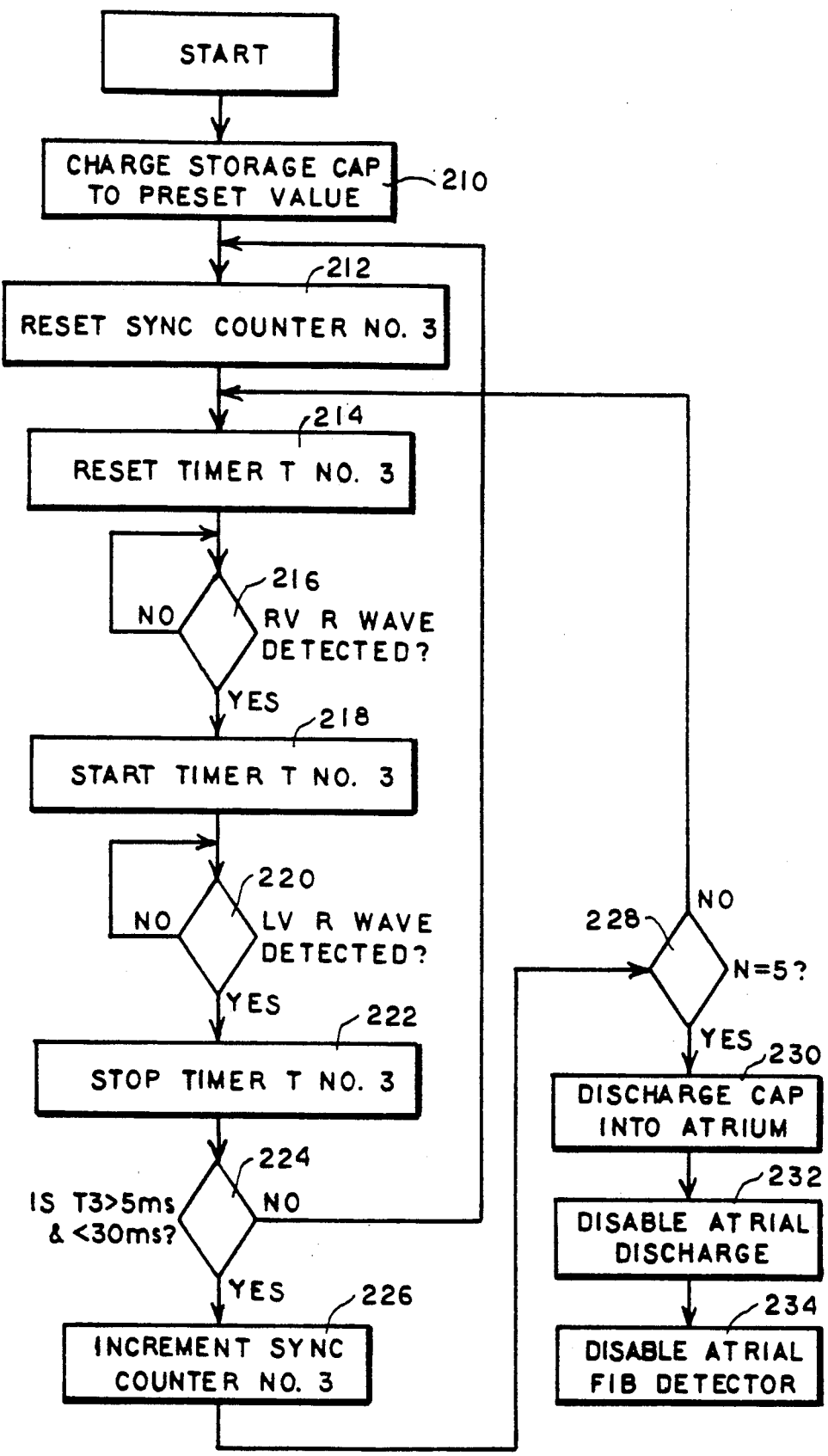
FIG. 6 is a flow diagram illustrating the manner in which the atrial defibrillator of FIG. 1 may be implemented in accordance with the present invention for providing defibrillating electrical energy to the atria of the heart in synchronism with detected electrical activations (R waves) of the heart.

Referring now to FIG. 6, it illustrates the manner in which the atrial defibrillator 30 may be implemented for applying cardioverting or defibrillating energy to the atria 16 and 18 of the heart 10. For this description, it is assumed that in step 178 the microprocessor determined that the atrial defibrillator was in the atrial defibrillating mode and that the charge delivery and energy control stage 90 had been activated by the microprocessor.

This process begins at step 210 with the charge delivery and energy control stage 90 providing over control line 111 an enable signal to enable the charger to charge the storage capacitor of the charger and storage capacitor circuit 110. The microprocessor then proceeds to step 212 to reset the third counter 88 which, as will be seen hereinafter, is utilized to count synchronizing pulses. The processor then proceeds to step 214 to reset the third timer 68. After resetting the third timer 68, the processor proceeds to step 216 to determine whether an R wave has been detected at the right ventricle. If an R wave has not been detected at the right ventricle, the microprocessor continues to determine whether an R wave has been detected at the right ventricle and when one is detected, the microprocessor proceeds to step 218 to start the third timer 68. After starting the third timer 68, the microprocessor proceeds to step 220 to determine whether the R wave has been detected at the left ventricle. If the R wave has not been detected at the left ventricle, the processor continues to determine whether the R wave has been detected at the left ventricle and when it is detected, the microprocessor in step 222 stops the third timer 68. After stopping the third timer 68, the microprocessor then in step 224 determines whether the detection of the R wave at the right ventricle and at the left ventricle occurred within the normal range of delay times of five milliseconds to 30 milliseconds. If it had not been so detected, the microprocessor then returns to step 212 to reset the third counter 88. If the R wave had been detected at the right ventricle and the left ventricle within the normal delay time, the microprocessor then proceeds to step 226 to increment the third counter 88. After incrementing the third counter 88, the microprocessor determines in step 228 if the third counter has reached a count of five. If it has not, the microprocessor returns to step 214 to once again reset the third timer 68 for detecting another electrical activation of the heart. When the third counter reaches a predetermined count of, for example, five counts, the microprocessor then proceeds to step 230 for discharging the capacitor of circuit 110. The discharging of the capacitor is controlled by the discharge circuit 112 and the discharge duration is determined by a signal carried on a control line 113 to control the duration of the discharge and thus the quantity of electrical energy delivered to the atria of the heart. The defibrillating or cardioverting energy is delivered between the second electrode 44 and the third electrode 46 of the second lead 36 to confine the cardioverting or defibrillating energy to the atria of the heart. The quantity of energy delivered to the atria for cardioverting or defibrillating the atria may be in the range of 0.1 to 3 joules. The actual quantity of defibrillating energy required will vary from patient to patient but, in the majority of the cases, will fall within the range of 0.1 to 3 joules.

After applying the defibrillating energy to the atria of the heart, the microprocessor then proceeds to step 232 to disable the charge delivery and energy control stage 90. Lastly, the microprocessor then proceeds to step 234 to disable the atrial fibrillation detector 82.

From the foregoing, it can be seen that five consecutive reliable synchronizing pulses must be provided by the sync detector 72 before defibrillating or cardioverting electrical energy is applied to the atria of the heart to assure reliable synchronization. Upon the fifth synchronizing pulse, the defibrillating or cardioverting electrical energy is then applied to the atria of the heart which will occur in synchronism with the last one of the predetermined number of electrical activations detected by the sync detector 72. As a result, reliable synchronization of the defibrillating or cardioverting electrical energy with a detected electrical activation of the heart will be assured.

Once the atrial fibrillation detector is disabled in step 234, the atrial defibrillator returns to once again determine the probability of atrial fibrillation and, if there is a probability of atrial fibrillation, to once again enable the atrial fibrillation detector. This begins the implementation of the atrial defibrillator as illustrated in the flow diagrams of FIGS. 4–6.

Figures 7, 8:
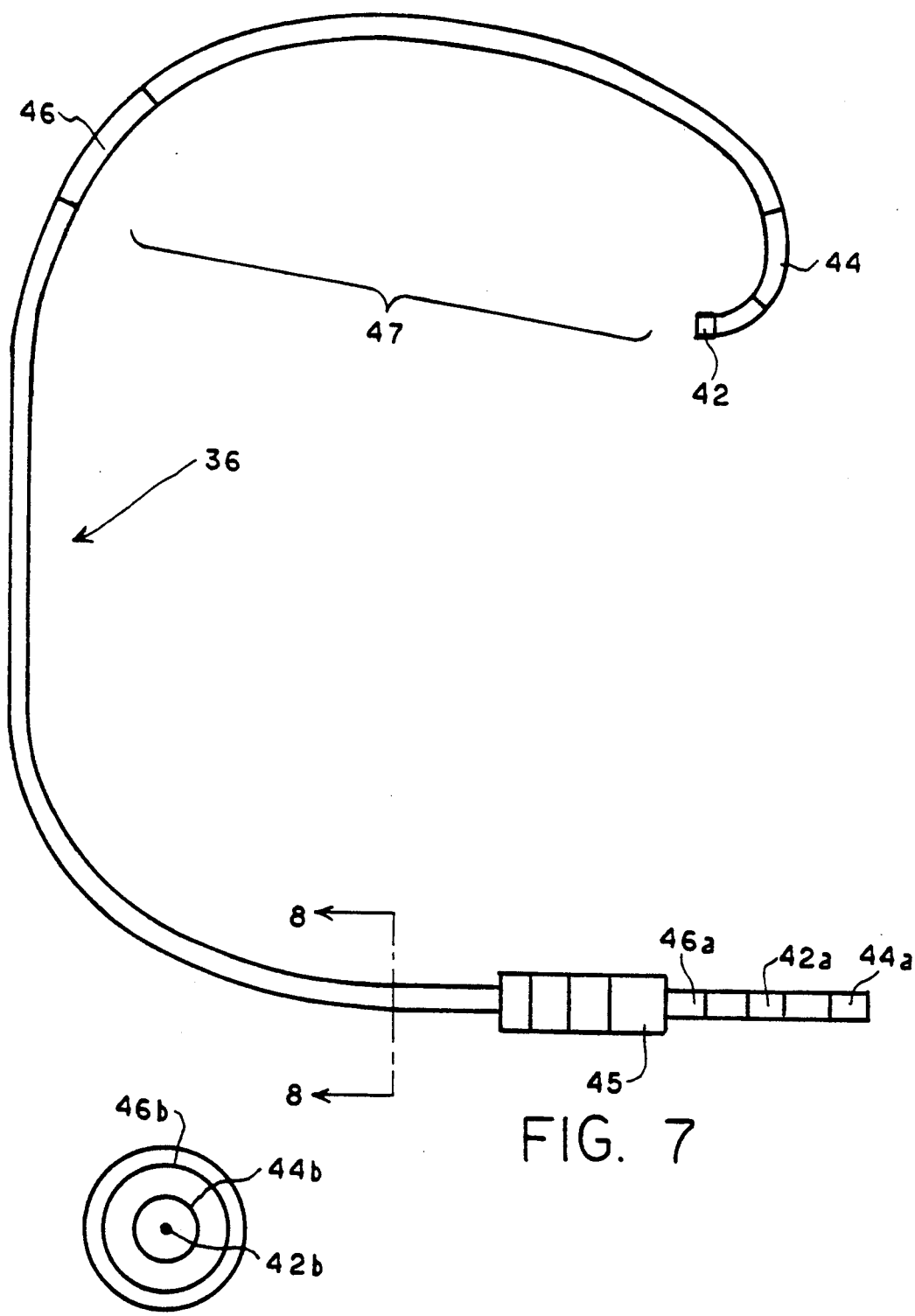
FIG. 7 is a top plan view illustrating an endocardial lead embodying the present invention having a plurality of electrodes for sensing electrical activations of the left ventricle, sensing electrical activations of the atria, and applying defibrillating electrical energy to the atria.
FIG. 8 is a cross-sectional view, to an enlarged scale, taken along lines 8—8 of FIG. 7.

Referring now to FIG. 7, it illustrates the intravascular second lead 36 which is structured in accordance with another aspect of the present invention. As will be noted, the lead 36 includes the first or tip electrode 42, the second or ring electrode 44, and the third electrode 46. Hence, the second electrode is proximal to the tip electrode 42, and the third electrode 46 is proximal to the second electrode 44 with the first electrode 42 being at the distal end of the lead.

The lead 36 also includes a connector 45 at its proximal end having a first contact 42a, a second contact 44a, and a third contact 46a. The connector 45 is preferably arranged for being matingly received by a complimentary receptacle of the enclosure 32 of the atrial defibrillator 30. The lead 36 includes three conductors which are illustrated in FIG. 8. Here it can be seen that the first conductor 42b, the second conductor 44b, and the third conductor 46b are coaxially disposed to one another with the first conductor 42b being a center conductor, the second conductor 44b being an inner conductor, and the third conductor 46b being an outer conductor. The conductors are arranged such that the first conductor 42b connects the first contact 42a with the first electrode 42, the second conductor 44b connects the first contact 44a with the second electrode 44, and the third conductor 46b connects the third contact 46a with the third electrode 46. It will also be noted that the lead 36, although being flexible, includes a preshaped portion and is preshaped to generally conform to the shape of the coronary sinus of the heart in which the lead is arranged to be advanced. The preshaping of the electrode in portion 47 assures that the distal end or tip electrode 42 will advance to within the coronary sinus adjacent the left ventricle. As previously mentioned, when the first electrode is within the coronary sinus adjacent the left ventricle, the second electrode 44 is beneath the left atrium near the left ventricle and the third electrode is within the right atrium or the superior vena cava.

From the foregoing, it can be seen that the present invention provides a new and improved fully implantable atrial defibrillator which is fully automatic. In addition, the atrial defibrillator of the present invention is arranged to conserve power to minimize the frequency in which a depletable power source must be replaced. In addition, the atrial defibrillator of the present invention assures reliable synchronizing of the defibrillating or cardioverting electrical energy to the atria with sensed electrical activations in the heart. Further, the atrial defibrillator of the present invention provides a means by which the reliable generation of synchronizing pulses may be confirmed. All of the foregoing assures that an atrial defibrillator is provided which is safe in use and has an extended lifetime.

While a particular embodiment of the present invention has been shown and described, modifications may be made, and it is therefore intended in the appended claims to cover all such changes and modifications which fall within the true spirit and scope of the invention.

What is claimed is:

1. A lead for use in association with an atrial defibrillator of the type arranged to cardiovert the atria of the human heart, said lead comprising:

a distal end and a proximal end, said proximal end including connector means arranged to be received by said atrial defibrillator, said connector means including first, second, and third contacts;

a first electrode at said distal end;

a second electrode proximal to said first electrode;

a third electrode proximal to said second electrode;

conductor means for electrically connecting said first contact to said first electrode, said second contact to said second electrode, and said third contact to said third electrode; and said lead being flexible so as to be arranged to be passed down the superior vena cava of the heart, into the right atrium, into the coronary sinus ostium, and advanced into the coronary sinus or great cardiac vein of the heart near the left ventricle, and wherein said electrodes are spaced apart such that when said first electrode is within the great cardiac vein adjacent the left ventricle, said second electrode is within the great cardiac vein or the coronary sinus adjacent the left atrium.

2. A lead as defined in claim 1 wherein said conductor means are coaxially disposed with said first conductor being a center conductor, said second conductor being an inner conductor, and said third conductor forming an outer conductor.

3. A lead as defined in claim 1 wherein the distal end beyond said third electrode is preshaped to generally conform to the shape of the coronary sinus of the heart.

4. A lead as defined in claim 1 wherein said second and third electrodes are cardioverting electrodes.

5. A lead for use in association with an atrial defibrillator of the type arranged to cardiovert the atria of the human heart, said lead comprising:

a distal end and a proximal end;

a first cardioverting electrode; and a second cardioverting electrode proximal to said first electrode, said lead being flexible so as to be arranged to be passed down the superior vena cava of the heart, into the right atrium, into the coronary sinus ostium, and advanced into the coronary sinus or great cardiac vein, and wherein said electrodes are spaced apart such that when said first electrode is within the coronary sinus or great cardiac vein adjacent the left atrium, said second electrode is within the right atrium or the superior vena cava and wherein the distal end of said lead beyond said second electrode is preshaped to generally conform to the shape of the coronary sinus of the heart.

* * * * *